United States Patent
Banet et al.

[19]

[11] Patent Number: 6,118,533
[45] Date of Patent: Sep. 12, 2000

[54] METHOD AND APPARATUS FOR MEASURING THE CONCENTRATION OF IONS IMPLANTED IN SEMICONDUCTOR MATERIALS

[75] Inventors: Matthew J. Banet, Cambridge, Mass.; John A. Rogers, Castle Rock, Colo.; Martin Fuchs, Uxbridge, Mass.

[73] Assignee: Active Impulse Systems, Inc., Mass.

[21] Appl. No.: 08/926,850

[22] Filed: Sep. 10, 1997

Related U.S. Application Data

[63] Continuation-in-part of application No. 08/885,786, Jun. 30, 1997.

[51] Int. Cl.$^7$ ....................................................... G01B 9/02
[52] U.S. Cl. ............................ 356/345; 356/432; 356/359
[58] Field of Search ..................................... 356/345, 359, 356/360, 432, 432 T

[56] References Cited

U.S. PATENT DOCUMENTS

| | | |
|---|---|---|
| 3,462,223 | 8/1969 | Tiemann et al. . |
| 4,522,510 | 6/1985 | Rosencwaig et al. . |
| 4,655,547 | 4/1987 | Heritage et al. . |
| 4,710,030 | 12/1987 | Tauc et al. . |
| 4,728,165 | 3/1988 | Powell . |
| 4,812,036 | 3/1989 | Inoue . |
| 4,939,368 | 7/1990 | Brown . |
| 5,062,693 | 11/1991 | Beratan et al. . |
| 5,132,824 | 7/1992 | Patel et al. . |
| 5,220,403 | 6/1993 | Batchelder et al. . |
| 5,263,039 | 11/1993 | Skupsky et al. . |
| 5,285,438 | 2/1994 | Marchand et al. . |
| 5,344,236 | 9/1994 | Fishman . |
| 5,361,638 | 11/1994 | Pettersson et al. . |
| 5,438,879 | 8/1995 | Reda . |
| 5,479,256 | 12/1995 | Tamai et al. . |
| 5,546,811 | 8/1996 | Rogers et al. . |
| 5,633,711 | 5/1997 | Nelson et al. ........................... 356/432 |
| 5,672,830 | 9/1997 | Rogers et al. . |
| 5,734,470 | 3/1998 | Rogers et al. . |

OTHER PUBLICATIONS

Rose et al., Picosecond Transient Grating Transport in Anthracene Single Crystals, Measurements of Singlet Excitation, Chem. Phys. Letters, 106:13–19, 1984.

Rao et al., "Picosecond Laser–Induced Transient Grating Probe of the Mechanical Properties of High–Modulus Poly(p–phenylenebenzobisoxazole–2.6–diyl)", Macromolecules, 22:985–989, 1989.

Rothenhausler, "Plasmon Surface Polariton Fields for the Characterization of Thin Films", Thin Solid Films, 159:323–330, 1988.

A.R. Duggal et al., "Real–time Characterization of Acoustic Modes of Polyimide Thin–Film Coatings Using Impulsive Stimulated Thermal Scattering", App. Phys. Lett., 60(6) Feb. 10, 1992, pp. 692–694.

Meth et al., "Experimental and Theoretical Analysis of Transient Grating Generation and Detection of Acoustic Waveguide Modes in Ultrathin Solids", J. App. Phys. 67:3362–3377, 1990.

(List continued on next page.)

*Primary Examiner*—Robert H. Kim

[57] ABSTRACT

A method and apparatus that determines a concentration of ions implanted in a material is described. The method includes the steps of: 1) generating at least two excitation laser sub-pulses and a probe pulse from a single pulse emitted from a laser; 2) irradiating a region of the material with a grating pattern formed by overlapping at least two excitation laser sub-pulses to initiate a time-dependent response in the region; 3) diffracting a probe laser pulse off the region to generate at least one time-dependent signal beam; 4) detecting at least one time-dependent signal beam to generate a signal waveform; and 5) processing the signal waveform to determine the concentration of ions implanted in the material.

30 Claims, 4 Drawing Sheets

OTHER PUBLICATIONS

Meth et al., "Generation and Detection of Acoustic Waveguide Modes in Ultrathin Crystals Using the Transient Grating Technique", Chem. Phys. Letters, 162:306–312, 1989.

Nelson et al., "Optical Generation of Tunable Ultrasonic Waves", J. App. Phys., 53:1144–1149, 1982.

Nizzoli, "Problem with the Determination of Elastic Constants from Higher–Order Surface Waves: Results for Al on NaCl", Physical Review B, 37:1007–1010, 1988.

Noll et al., "Picosecond Photoinduced Index Changes in a Si:H and Related Alloys Measured by Transient Grating Experiments", J. Non–Crystalline Solids, 97 & 98:141–144, 1987.

Portella et al., "Four–Wave Mixing Experiments in Cresyl Violet Thin Films: Inadequacy of a Two–Level Interpretation", J. Phys. Chem., 91:3715–3719, 1987.

Prasad, "Non–Linear Optical Effects in Thin Organic Polymeric Films", Thin Solid Films, 152:275–294, 1987.

Rao et al., "Third Order Nonlinear Optical Interactions in Thin Films by Poly–p–phenylenebenzobisthiazole Polymer Investigated by Picosecond and Subpicosend Degenerated Four Wave Mixing", App. Phys. Letters, 48:1187–1189, 1986.

Rao et al., "Picosecond Transient Grating Studies of Polymeric Thin Films", App. Phys. Letters, 48:387–389, 1986.

Rogers et al., "Real–Time In Situ Characterization of Thin Films", CHEMF. 8, 27 (1992), pp. 4–8.

Whitman et al., Appl. Optics, 8, 1567 (1969).

Nizzoli et al., Dynamical Properties of Solids (ed. G.K. Horton et al., North–Holland Amsterdam, 1990) vol. 6, 283.

Bortolani et al., J. Phys. C., 16, 1757 (1983).

Fishman I.M. et al., "Surface Selectivity in Four–Wave Mixing: Transient Gratings as a Theoretical and Experimental Example", J. Opt. Soc. Am. B., vol. 8, No. 9, Sep. 1991, pp. 1880–1888.

Barish et al., "Photoinduced Ionization of Bovine Serum Albumin by Holographic Relaxation Methods", J. Chem. Phys. 85:4194–4195, 1986.

Burzynski et al., "Study of Anisotrophy of Acoustic Wave Propagation in Stretched poly(vinylidene difluoride) Film Using the Picosecond Transient Grating Technique", Polymer, 30:1247–1250, 1989.

Deeg et al., "New Grating Experiments in the Study of Irreversible Photochemical Reactions", IEEE J. Quantum Electronics, QE–22:1476–1481, 1986.

Espinet et al., "Laser–induced Gratings in Nematic/Cholesteric Mixtures", App. Phys. Letters, 50:1924–1926, 1987.

Greene et al., Picosecond Relaxation Dynamics in Polydiacetylene–pTs, Chem. Phys. Letters, 139:381–385, 1987.

Duggal et al., "Resolution of Conflicting Descriptions of Propylene Glycol Relaxation Dynamics Through Impulsive Stimulated Scattering Experiments", Polymer Communications, 32:356–360, 1991.

Duggal et al., "Real–Time Optical Characterization of Surface Acoustic Modes of Polymide Thin–Film Coatings", J. Appl. Phys. 72:2823–2839, 1992.

Fishman et al., "Surface Selectivity in Holographic Transient Grating–Diffraction", Stanford University, Stanford, CA; W.W. Hansen Exp. Phys. Lab. & Dept. of Chemistry.

Goldsmith et al., "Measurement of Stresses Generated to Cured Polyimide Films", J. Vac. Sci. Technol. 1:407–409, 1983.

Head et al., "Determination of Shear Stress at a Solder Paste/Stencil Interface", Mat. Res. Soc. Symp. Proc. 323:425–433, 1994.

Maden et al., "Stress Analysis of Thin Polyimide Films Using Holographic Interferometry", Experimental Mechanics 31:179–184, 1991.

Rogers et al., "Study of Lamb Acoustic Waveguide Modes in Unsupported Polyimide Thin Films Using Real–Time Impulsive Stimulated Thermal Scattering", J. Appl. Phys. 75:1534–1556, 1994.

Duggal, "Picosecond–Microsecond Structural Relaxation Dynamics in Polypropelyne Glycol", Journal of Chemical Physics, No. 94, pp. 7677–7688, Jun. 15, 1991.

Allen et al., "Microfabricated Structures for the in situ Measurement of Residual Stress, Young's Modulus, and Ultimate Strain of Thin Films", Appl. Phys. Lett., 51:241–243, 1987.

Bauer et al., "Determination of the Stresses and Properties of Polymer Coatings", J. of Coatings Technology, 60:51–55, 1988.

Coburn et al., "Stress in Polyimide Coatings", J. of Polymer Science: Part B: Polymer Physics, 32:1271–1283, 1994.

Washidzu et al., Dose and Damage Measurements in Low Dose Ion Implantation in Silicon by Photo–Acoustic Displacement and minority Carrier Lifetime, Jap. J. Appl. Phys. vol. 30 (1991), No. 6A, pp. 1025–1027.

Harata et. al., Transient Reflecting Grationg Study of Ion–Implanted Semiconductors, Journ. De Phys. IV. Colloque C7 (1994), p. C7–159.

Harata, et al., Laser–Stimulated Scattering Microscopc Study of an Ion–Implanted Silicon Surface, Jpn. J. Appl. Phys. vol. 32 (1993) Pt. 1, No. 8, pp. 3633–3638.

Harata, et al., Laser–Induced Surface Acoustic Waves and Photothermal Surface Gratings Generated by Crossing Two Pulsed Laser Beams, Appl. Phys. Lett. vol. 57 (1990), Pt. 2, No. 9, pp. 2, No. 9, pp. 132–134.

Shen, et al., Analysis of the Thermal and Acoustic Properties of Ion–Implanted Diamond–Like Carbon Films Using the Transient Reflecting Grating Technique, J. Appl. Phys. vol. 77 (1995), No. 4, pp. 1488–1491.

METHOD AND APPARATUS FOR MEASURING THE CONCENTRATION OF IONS IMPLANTED IN SEMICONDUCTOR MATERIALS This application is a continuation-in-part of METHOD AND DEVICE FOR MEASURING THE CONCENTRATION OF IONS IMPLANTED IN SEMICONDUCTOR MATERIALS (U.S. Ser. No. 08/885,786; filed Jun. 30, 1997), the contents of which are incorporated herein by reference.

BACKGROUND

This invention relates to measuring the concentration of ions implanted in semiconductor materials.

Most microelectronic devices (e.g., microprocessors) include a series of thin insulating (e.g. oxide) and conducting (e.g., metal and polysilicon) films grown or deposited on a single-crystal silicon wafer. Both silicon wafers and polysilicon films are implanted with ions during fabrication so that they exhibit a specified electrical conductance. For example, the silicon may be implanted to create regions that function as a "p" or "n" type semiconductor. After implantation, both silicon and polysilicon are annealed under high temperatures to heal lattice damage that typically results from the implantation process.

The electrical conductance of silicon and polysilicon is strongly affected by three properties of the implanted ions: (1) atomic composition; (2) implantation energy; and (3) ion concentration or dose. Silicon's electrical conductivity is particularly dependent on the concentration of the implanted ions. For example, silicon wafers are typically implanted with arsenic, argon, phosphorous, oxygen, or boron ions ranging in concentration from $10^{12}$–$10^{16}$ cm$^{-3}$. These ions are typically implanted with energies ranging from a few keV to thousands of keV.

The performance of a completed microelectronic device depends critically on the electrical properties of the silicon wafer and the overlying polysilicon films, and thus the properties of ions implanted in these materials are carefully monitored during fabrication. One property, called electrical sheet resistance, is measured by contacting a sample's surface with an electrical-testing instrument called a 4-point probe. Electrical current flowing from one probe to another depends on the resistance of the material. Resistance, in turn, varies inversely with the concentration of implanted ions.

Ion concentration is also monitored using a non-contact, optical method that excites and detects both a photothermal response and an electron-hole plasma within the silicon. To make this measurement, a first laser beam irradiates the silicon and is partially absorbed to generate either (or both) the electron-hole plasma and photothermal response. These responses modify the reflectivity of the sample's surface and are measured with a second laser beam. This is partially reflected by the sample and then analyzed to estimate the concentration of the implanted ions.

Although used throughout the microelectronics industry to determine the concentration of implanted ions, both 4-point probes and instruments that measure optical reflectivity suffer disadvantages. 4-point probes necessarily contact the sample, and are therefore destructive. This means that these instruments can only measure "monitor" wafers or regions of "product" wafers that lack functioning devices. In addition, 4-point probes can only measure annealed wafers. Optical-reflectivity instruments have a limited scope of measurement and generate signals that are often difficult to interpret: they are therefore used primarily to determine whether or not a sample has been ion implanted with ions, rather than the actual concentration of the implanted ions.

SUMMARY

The method and apparatus described herein measure the concentration of ions implanted within a semiconducting material with a non-contact, laser-based technique called four-wave mixing (FWM). In the applications described herein, FWM is carried out with a single laser. This allows measurement of samples that have been difficult or impossible to measure with the two-laser systems described previously.

FWM initiates an optical response in a semiconducting material with two laser beams. These beams, which have wavelengths that are strongly absorbed by the sample, are overlapped in time and space on the sample's surface to form a grating pattern. Each laser beam includes pulses that typically have a duration of less than 1 nanosecond. Absorption of the pattern generates a time-dependent change in the sample's refractive index, resulting in a response that rapidly increases in amplitude and then decays away in a few nanoseconds. A third laser beam irradiates the grating pattern and is diffracted to form a fourth signal beam. The amplitude of the signal beam depends on the concentration of the ions implanted in the semiconductor material. This concentration can then be analyzed and used to control fabrication processes used to make microelectronic devices.

In one aspect, the invention provides a method that determines a concentration of ions implanted in a material. The method includes the steps of: 1) generating at least two excitation laser sub-pulses and a probe pulse from a single pulse emitted from a laser; 2) irradiating a region of the material with a grating pattern formed by overlapping at least two excitation laser sub-pulses to initiate a time-dependent response in the region; 3) diffracting a probe laser pulse off the region to generate at least one time-dependent signal beam; 4) detecting at least one time-dependent signal beam to generate a signal waveform; and 5) processing the signal waveform to determine the concentration of ions implanted in the material.

In another aspect, the method includes the step of generating a single laser pulse, and then passing the laser pulse through a diffracting mask to form at least two excitation sub-pulses and at least one probe pulse. Both excitation and probe pulses then irradiate the sample as described above to measure the concentration of ions implanted in the semiconductor. Here, a single pulse may function as both the excitation sub-pulse and the probe pulse (i.e., self diffraction).

In certain embodiments, the processing step described above includes determining a property of the signal waveform (e.g., an amplitude) and then processing the property to determine the concentration of ions implanted in the sample. The processing step may include comparing the property of the signal waveform to a database, e.g., a database that correlates properties of previously measured signal waveforms to concentrations of implanted ions. In other embodiments, the processing step includes analyzing the amplitude with a mathematical algorithm to determine the concentration of ions implanted in the material. The processing step can also include digitizing the signal waveform to generate a data set, and then determining the amplitude of the signal waveform at a point in time by selecting a value from the data set. In still other embodiments, the processing step includes determining an area covered by a plot of the signal waveform, and then comparing the area to a database similar to that described above.

The above-described method and apparatus determines the concentration of ions implanted in different types of host samples. These samples include semiconducting materials, such as silicon-containing (e.g. polysilicon) films, silicon wafers, and films and wafers containing gallium arsenide, aluminum gallium arsenide, germanium, and derivatives and analogies thereof. Other samples that can be measured include ceramic materials, metals, and any other material that can be implanted with ions. The ion implanted in the material is typically an ion of an atom selected from the group including arsenic, argon, boron, oxygen and phosphorous atoms.

The method of the invention is carried out with an apparatus that includes: 1) a single laser that generates an excitation laser pulse and a probe laser pulse; 2) a first beam-delivery system that separates the excitation laser pulse into at least two sub-pulses and then irradiates a region of the material with a grating pattern formed by overlapping at least two sub-pulses; 3) a second beam-delivery system that delivers the probe pulse to the sample such that it diffracts off the region to generate a time-dependent signal beam; 4) a photodetector that detects the time-dependent signal beam to generate a signal waveform; and 5) a processor that processes the signal waveform to determine the concentration of ions implanted in the material.

In typical embodiments, the first beam-delivery system includes a diffracting mask (e.g., a phase or amplitude mask) that separates the excitation laser pulse into at least two sub-pulses. The processor is typically a computer that analyzes an amplitude of the signal waveform and then compares the amplitude to a database to determine the concentration of ions implanted in the material. Alternatively, the computer determines an area covered by the signal waveform, and then compares the area to a database to determine the concentration of ions implanted in the material. In typical embodiments, the excitation sub-pulses and the probe pulse are overlapped in time in the region, and the photodetector has a bandwidth of less than 1 MHz.

Another apparatus that carries out the method of the invention includes a single laser and a beam-delivery system that includes a diffracting mask that separates the laser pulse into at least two excitation sub-pulses and a probe pulse. The system also includes a lens that focuses and overlaps the two excitation sub-pulses and the probe pulse on the sample. In this embodiment, the sub-pulses form a grating pattern that initiates a time-dependent response in the region and the probe pulse diffracts off the region to generate a time-dependent signal beam.

The above-described method and apparatus have many advantages when compared to conventional techniques for measuring the concentration of implanted ions. In general, FWM is an accurate, quantitative method for determining the concentration of ions implanted in both semiconductor substrates and thin films. The method is all-optical, non-contact, and non-destructive, and can therefore measure semiconductor materials used in actual devices (i.e., production samples), rather than monitor samples. This information can then be used by manufacturers to improve both the yield and performance characteristics of microelectronic devices containing these materials. In addition, the single-laser apparatus for making FWM measurements generates signal waveforms having very high signal-to-noise ratios and the apparatus has a large dynamic range of measurement. This apparatus accurately measures samples, such as silicon wafers implanted with boron ions at low energies and concentrations, that in the past have been difficult to measure with conventional instrumentation, such as those using two lasers. Moreover, this instrument is compact, easily automated, has very few optical elements, and is relatively inexpensive to manufacture. Since the concentration of implanted ions can be measured in this way, it is not necessary to determine the waveform's time dependence. This signal amplitude can be measured with simple optical and electrical components (e.g., low-bandwidth photodetectors and analog-to-digital converters) that are typically low-cost and commercially available.

Another advantage is that the phase mask simplifies the alignment of the excitation and probe laser beams and also eliminates the need for additional beam-delivery optics, such as additional lenses and beam splitters, that are normally required for FWM experiments. The number of required optical elements is even further reduced in embodiments where the phase mask diffracts an incident laser pulse to form both the excitation sub-pulses and the probe pulse.

Measurements with the above-mentioned apparatus are made rapidly (typically requiring only a few seconds) and with high spatial resolution (typically using a probe beam having a spot size of about 50 microns or less). Thus, small features of the sample, such as a small-scale test site of a microelectronic device or an area near a wafer's edge, can be easily measured. Moreover, the above-mentioned apparatus can be incorporated into a facile, compact, easy-to-use instrument that can be employed in a microelectronic-device fabrication facility. The instrument, for example, can be attached to a production tool and used to make in situ measurements of an ion-implantation process.

Still other advantages will be apparent from the following detailed description, and from the claims.

DETAILED DESCRIPTION

Method for Measuring Ion Implantation Concentration with FWM

Figure 1:
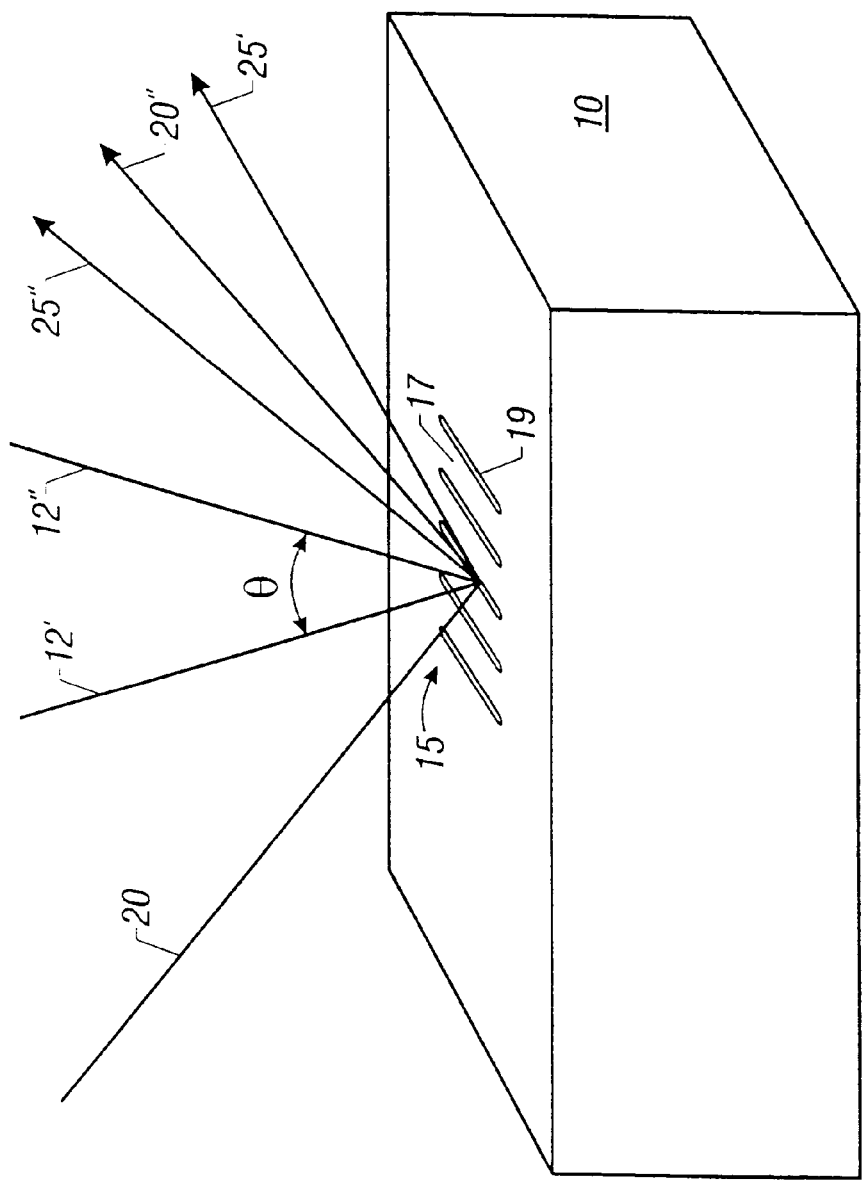
FIG. 1 is a schematic drawing of the FWM method.

Referring to FIG. 1, the concentration of ions implanted in a sample 10 (e.g., a silicon wafer) is measured with an optical, laser-based technique called four-wave mixing (FWM). Applicants have described the use of related laser-based techniques, called impulsive stimulated scattering (ISS) and impulsive stimulated thermal scattering (ISTS), to measure other material properties in MEASUREMENT OF MATERIAL PROPERTIES WITH OPTICALLY INDUCED PHONONS (U.S. Pat. No. 5,633,711); SIMPLIFIED DEVICE AND METHOD FOR TIME-RESOLVED OPTICAL MEASUREMENTS (U.S. Ser. No. 08/377,310; filed Jan. 24, 1995); METHOD AND DEVICE FOR MEA- SURING FILM THICKNESS (U.S. Ser. No. 08/783,046; filed Jun. 15, 1996); IMPROVED METHOD AND APPARATUS FOR MEASURING MATERIAL PROPERTIES USING TRANSIENT GRATING SPECTROSCOPY (U.S. Ser. No. 08/885,555; filed Jun. 30, 1997); and METHOD AND APPARATUS FOR MEASURING THE CONCENTRATION OF IONS IMPLANTED IN SEMICONDUCTOR MATERIALS (U.S. Ser. No. 08/885,786; filed Jun. 30, 1997), all of which are incorporated herein by reference.

In FWM, a pair of optical excitation sub-pulses 12', 12" from a laser (not shown in the figure) separated by an angle θ are overlapped in time and space in a region on the sample's surface. Interference between the overlapped sub-pulses 12', 12" forms a spatially varying "grating" pattern 15 containing alternating "light" (constructive interference) 17 and "dark" (destructive interference) 19 regions. The sample 10 absorbs radiation in the light regions 17, but not in the dark regions 19 of the grating pattern 15. The absorbed radiation initiates a time-dependent response characterized by an amplitude that depends on the concentration of the ions implanted in the sample 10. This response is measured by irradiating a region near the grating pattern 15 with a probe pulse 20 generated by the same laser that generates the excitation sub-pulses 12', 12". The probe pulse 20 is overlapped in time and space with these sub-pulses on the sample's surface. This means that prior to irradiating the sample, the distance traveled by the excitation sub-pulses and the probe pulse after leaving the single-laser source is roughly equivalent. When these three pulses are overlapped in this way, the probe pulse is partially reflected to form a reflected beam 20", and partially diffracted to form a pair of signal beams 25', 25" that are the +1 and −1 diffracted orders. One or both of the signal beams 25', 25" is detected with a photodetector (not shown in the figure) to generate a signal waveform. The amplitude of the signal waveform is then analyzed to determine the concentration of the implanted ions.

The excitation sub-pulses 12', 12" typically have a duration of between 0.3–0.7 nanoseconds (i.e., $0.3–0.7 \times 10^{-9}$ seconds), an energy of about 2 microjoules/pulse, and a wavelength that is partially absorbed by the sample. For silicon, the wavelength is typically in the visible spectral region (e.g., 532 nm). Since it is generated with the same laser, the probe pulse has the same wavelength and duration as the excitation pulse. The energy of the probe pulse is typically between 0.25 and 1.0 microjoules.

FWM generates a response in the sample when the excitation radiation has an energy that is above the band gap of the sample (for silicon, this is about 1.1 eV, an energy that corresponds to an optical wavelength of or 900 nm). Without being bound to any theory, it appears that in this case the excitation pattern in FWM generates excited-state charge carriers (e.g., electron-hole pairs) in the light regions, but not the dark regions of the grating pattern. The density of charge carriers depends on the concentration of ions implanted in the sample. Once generated, the charge carriers have a finite lifetime and recombine with a time constant on the order of several nanoseconds. During this period the sample's refractive index in the light regions is temporarily changed relative to the refractive index in the dark regions. This results in a spatially periodic variation in refractive index (i.e., a phase grating) that diffracts probe radiation impinging on the sample during the lifetime of the charge carriers. The diffraction efficiency is highest immediately after the charge carriers are formed, and thus the probe pulse is arranged to impinge on the sample at essentially zero time delay (i.e., the excitation sub-pulses and probe pulse are overlapped in time). A higher concentration of implanted ions results in a larger number of excited charge carriers and, consequently, a greater difference in refractive index between the light and dark regions of the grating pattern. This, in turn, increases both the diffraction efficiency of the phase grating and the intensity of the diffracted probe beam.

Figure 2:
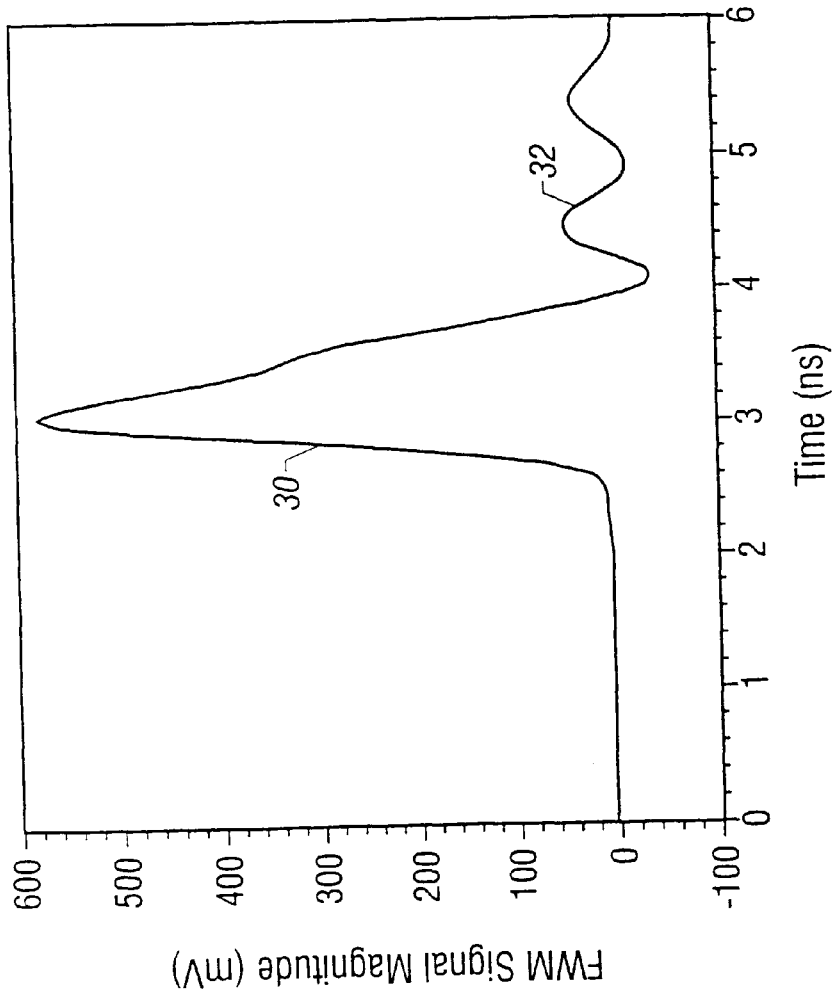
FIG. 2 is a graph of a signal measured during FWM with a single-laser optical system.

FIG. 2 shows a signal waveform 30 measured during FWM from a boron-implanted silicon wafer. The film was implanted with an average concentration of approximately $0.5 \times 10^{14}$ cm$^{-3}$ boron ions at an energy of about 20 keV. Measurements were made with excitation sub-pulses having a wavelength of 532 nm, a duration of about 0.5 nanoseconds, and an energy of about 2.0 microjoules/sub-pulse. The sub-pulses were generated by frequency-doubling the fundamental output from a Nd:YAG laser, and then passing this output through a phase mask (described in more detail with reference to FIG. 4). The probe pulse was generated by the same laser, and had an energy of about 0.5 microjoules/pulse. The optical path length traveled by the excitation and probe pulses was roughly identical. The signal waveform was measured with a photodetector and analog-to-digital converter that in combination have a bandwidth of about 1 GHz.

As is clear from the data, the signal waveform 30 rises rapidly and then decreases in intensity to form a spike having an asymmetric shape. The full-width half-maximum (FWHM) of the spike is roughly equal to the duration of the excitation and probe pulses (about 0.5 ns). The amplitude of the signal waveform, shown as being about 575 mV, depends on the concentration of ions implanted in the silicon sample ($0.5 \times 10^{14}$ cm$^{-3}$ in this case). The signal waveform also includes an oscillatory component 32 that is due to an electronic "ringing" in the photodetector. Although measured in this experiment with a relatively high-bandwidth detection system (1 GHz), the amplitude of the waveform 30 could also be extracted with a much simpler system, e.g., a photodetector and analog-to-digital converter with a bandwidth of less than 1 MHz.

Figure 3B:
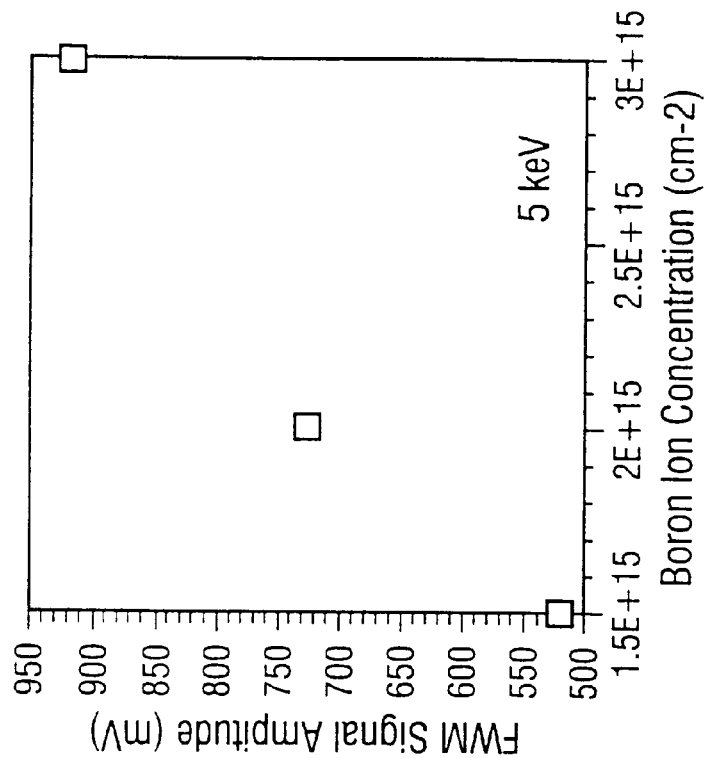
FIGS. 3A–3B are graphs of the signal waveform amplitude (in mV) vs. the ion implant concentration measured from a set of silicon wafers implanted with different concentrations of boron ions at 3 and 5 keV.
Figure 3A:
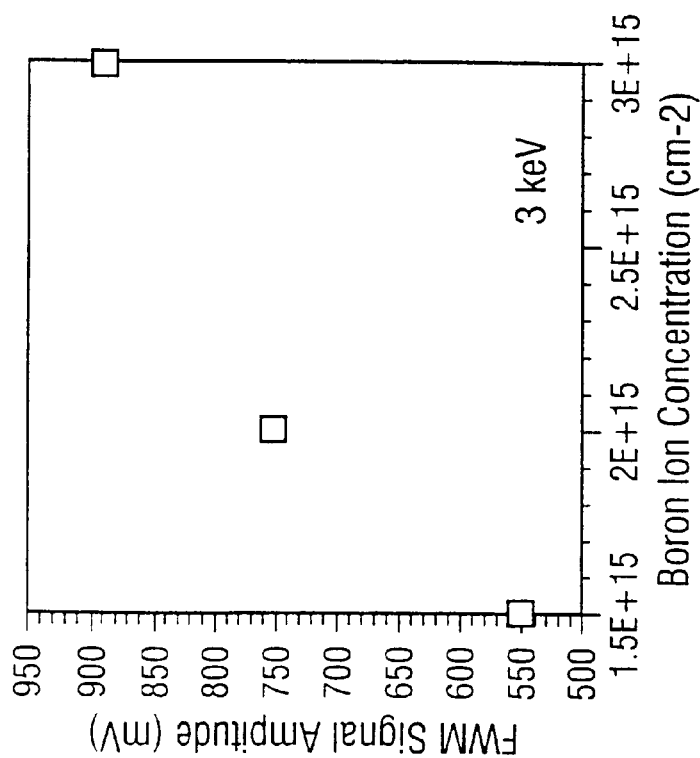

FIGS. 3A and 3B show how the amplitude of the signal waveform varies with the concentration of implanted ions. In these experiments, electronic responses were measured from a set of 100-mm diameter silicon wafers implanted with boron ions ranging from $1.5–3.0 \times 10^{15}$ cm$^{-3}$. The implant energies for FIGS. 3A and 3B were, respectively, 3 and 5 keV. The data were measured from a center point of each wafer using FWM and the same single-laser instrument described above. The data show that the signal waveform amplitude increases systematically with the concentration of implanted ions for each of the implantation energies. Similar dependencies of signal waveform amplitude on ion concentration were observed with boron, arsenic, oxygen, and phosphorous ions implanted in silicon wafers at energies ranging from 1–1000 keV and concentrations ranging from $1.0 \times 10^{12}$ to $1.0 \times 10^{16}$ cm$^{-3}$. Typically, silicon wafers with ions implanted at concentrations of $1.0 \times 10^{12}$ cm$^{-3}$ display signal levels of a few hundred mV, while wafers implanted with ions implanted at concentrations of $1.0 \times 10^{16}$ cm$^{-3}$ have signal levels of about 1000 mV.

In a typical embodiment, data like that shown in FIGS. 3A–3B is measured from a set of samples which vary systematically in one or more properties (e.g., concentration), and then stored in a database on a computer. The dependence of signal amplitude on concentration may depend on process conditions such as implant species, temperature, current, and orientation of the wafer relative to the incident ion beam. Thus, separate databases, each containing a data set similar to that shown in FIGS. 3A–3B, is typically generated for each process condition. To do this, the data can be measured from a set of test samples having a systematically varying concentration of implanted ions whose concentrations are verified with electrical testing instruments, such as a 4-point probe. During an actual measurement, the amplitude of a signal waveform is measured with FWM as described above, and then compared to a value in the appropriate database. This determines the concentration of ions implanted in a sample during an actual fabrication process.

Apparatus for Determining Ion Implant Properties Using FWM

Figure 4:
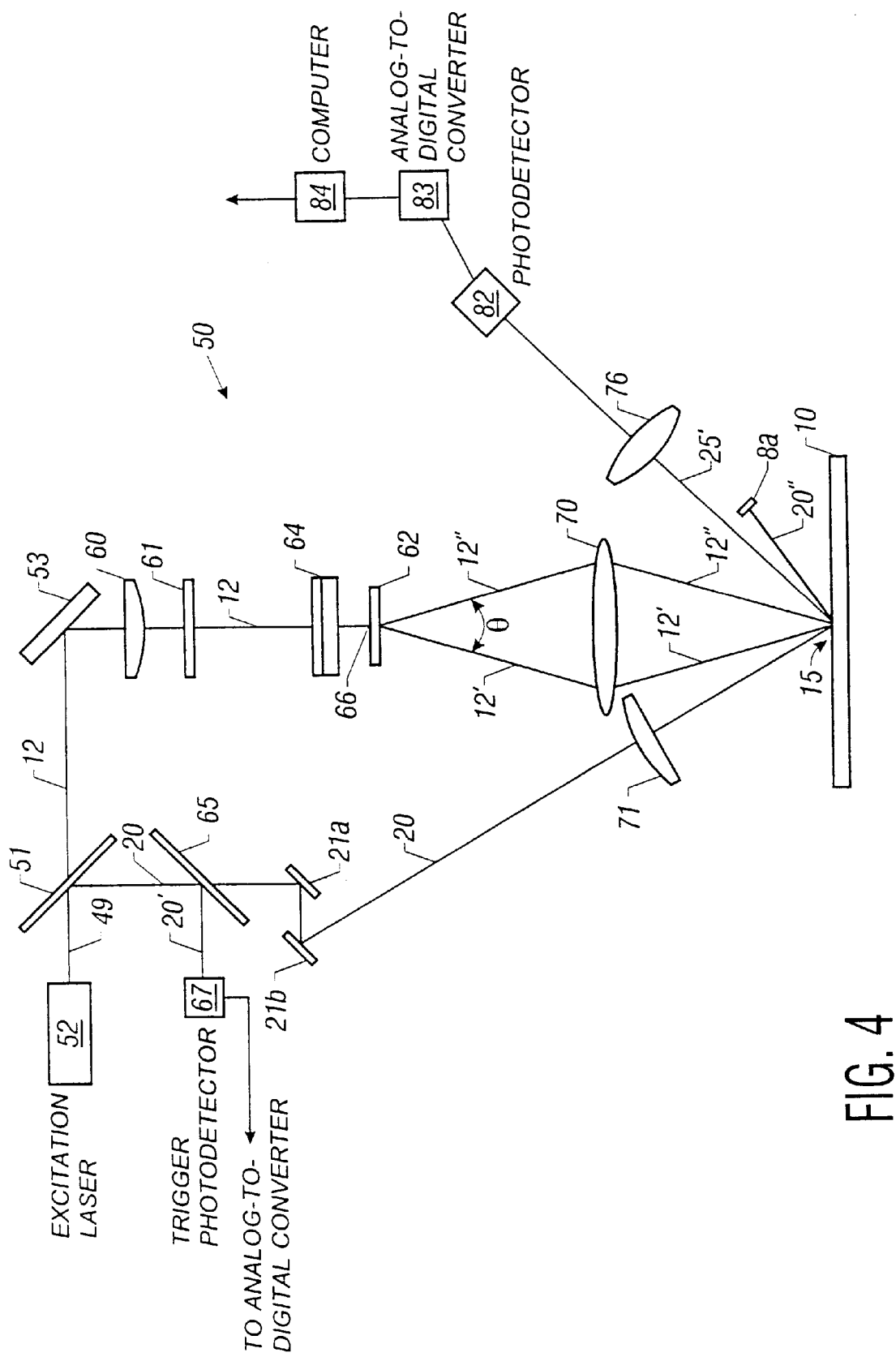
FIG. 4 is a schematic drawing of a single-laser optical system for measuring the concentration of ions implanted in a sample using FWM.

FIG. 4 shows an optical system 50 for measuring the properties of an ion-implanted sample 10 using FWM. The system 50 includes a single laser 52, such as a Nd:YAG laser, that generates a pulse 49 having the optical properties described above. Once generated, the pulse 49 irradiates a beamsplitter 51 that partially reflects a small portion (e.g. typically 5–15%) of the pulse 49 to form a probe pulse 20, and transmits the remainder of the pulse 49 to form the excitation pulse 12. The excitation pulse 12 then irradiates a mirror 53 that reflects it through a first collimating lens 60 and then through a neutral-density filter 61 used for adjusting the pulse energy. The pulse is then focused onto a phase mask 62 with a cylindrical lens 64. The phase mask 62 includes a series of patterns 66, each of which is capable of generating a different grating pattern 15 on the sample 10. The appropriate pattern is selected to produce the desired grating pattern on the sample. After selecting the appropriate pattern 66 on the phase mask 62, the excitation pulse 12 is diffracted into two sub-pulses 12', 12" that diverge at an angle θ determined by the selected pattern 66. The diverging sub-pulses 12', 12" are collected with a first imaging lens 70 that focuses and overlaps them onto the surface of the sample 10 to form the grating pattern 15. The first imaging lens 70 is positioned so that the grating pattern 15 has one half of the periodicity of the pattern 66 on the phase mask 62. Different grating patterns can be formed simply by translating the phase mask 62 so that a new pattern is irradiated with the incident excitation pulse 12.

Note that the probe pulse 20 is split prior to the collimating lens 60, and thus it spatially diverges over its optical path length, thereby allowing the pulse 20 to be focused to a smaller spot on the sample. A portion 20' of the pulse 20 is reflected by a beam-splitter 65 and detected with a trigger photodetector 67 to generate an electrical pulse for triggering a data-acquisition system. The portion of the probe pulse 20 that passes through the beam-splitter 65 is reflected by a pair of mirrors 21a, 21b and then focused on the grating pattern 15 with a second spherical lens 71 to measure the ion-implanted sample 10. The spacing between the mirrors 21a, 21b is adjusted so that the optical path lengths of the excitation sub-pulses (12' and 12") and the pulse probe 20 are approximately equal. This overlaps these pulses in time on the sample's surface, thereby ensuring that the maximum signal amplitude (which occurs at zero delay of the probe pulse) will be measured.

Once irradiated, the sample diffracts a portion of the probe pulse 20 to form a signal beam 25'. A beam-stop 80 blocks a reflected portion of the probe pulse 20". A second imaging lens 76 collects the signal beam 25' and focuses it into a high-speed (e.g., 1 GHz) photodetector 82. This generates a light-induced electrical signal which is then passes through an analog-to-digital converter 83 to produce a digital signal that is analyzed by a computer 84 which is programmed with an analysis algorithm to determine the concentration of ions implanted in the sample. The analysis algorithm is stored in a computer readable medium from where it is loaded in executable form into RAM memory of the computer.

The spatial dimensions of the excitation sub-pulses 12', 12" and probe pulse 20 focused onto the sample are chosen to maximize the amplitude of the signal waveform. The excitation sub-pulses are typically overlapped to form an elliptical grating pattern with the long and short axes of the ellipse being roughly 150 and 25 microns, respectively. The distance between light and dark regions in the grating pattern is typically between 5 and 15 microns. The probe pulse is typically focused to a round spot that lies completely within the grating pattern. For example, the probe pulse can be focused to a round spot with a diameter of less than 25 microns.

Other Embodiments

Figure 5:
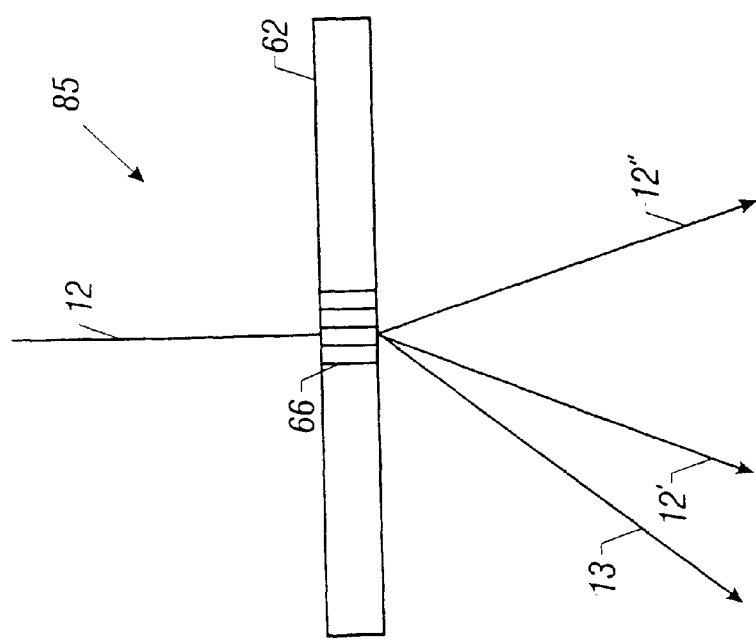
FIG. 5 is a drawing of a single laser beam being diffracted to form two excitation sub-pulses and a probe pulse.

Other embodiments are within the scope of the above-described method and apparatus. For example, different optical systems, such as one including: 1) a different lens configuration than that described above; 2) an amplitude mask in place of the phase mask; or 3) a beamsplitter in place of the phase mask, can be used. FIG. 5 shows another optical configuration 85 for generating both excitation sub-pulses 12', 12" and a probe pulse 13 from a single laser beam. In this case, a single pulse 12 from a laser (not shown in the figure) irradiates a pattern 66 on a phase mask 62 as described above. The pattern is chosen so that a majority (e.g., 85%) of the pulse 12 is diffracted into the +/−1 orders to form the excitation sub-pulses 12', 12". The portion of the incident pulse 12 diffracted into the +2 (or −2) order forms the probe pulse 13. The excitation sub-pulses 12', 12" and probe pulse 13 are collected with a single lens (such as lens 70 in FIG. 4) and then focused onto the sample as described above to measure the ion implantation concentration. In still other embodiments, a mirror may be inserted into the optical system shown in FIG. 5 to reflect the probe pulse through the lens and toward the sample.

In another optical system, described in IMPROVED METHOD AND APPARATUS FOR MEASURING MATERIAL PROPERTIES USING TRANSIENT GRATING SPECTROSCOPY (U.S. Ser. No. 08/885,555; filed Jun. 30, 1997), three sub-pulses, rather than two, are used to excite the sample in a FWM arrangement. In this optical system, the three sub-pulses are equally spaced in a linear fashion (i.e., the center, right, and left beams) prior to being imaged onto the sample. When focused with a lens, the center beam propagates down a central optical axis of a beam-delivery system, while the right and left beams converge toward the same spot at the same angle but on opposite sides of the center beam. The beams are overlapped on the sample to form the grating pattern that excites charge carriers in the sample.

In general, any optical system for performing ISS, ISTS or FWM is suitable to measure the concentration of implanted ions using the method described above. Likewise, other lasers that have suitable optical properties can be used in place of the Nd:YAG laser described above.

In other embodiments, FWM measurements can be performed using two synchronized lasers in place of the single laser described above. Each of the synchronized lasers generates a short (e.g., 0.5 ns) optical pulse, one which represents the excitation pulse, and the other laser which represents the probe pulse. As described above, the resulting two laser beams are oriented so that pulses are overlapped in time on the sample's surface.

In still other embodiments, the system uses multiple probe pulses, each of which is delayed in of time relative to the others, to measure a decay time constant of the excited charge carriers. For example, the system uses a first probe pulse to irradiate the sample at zero time delay, and then it uses a second pulse, which is mechanically delayed, to irradiate the sample a few nanoseconds later. The first pulse will produce a signal having a given amplitude and the second, later pulse will produce a signal having a lower amplitude. The change in amplitude represents a decay process (e.g. exponential decay process) that can be characterized by a time constant. The computer analyzes the two signal waveforms generated by the two probe pulses and determines the decay time constant for the charge carriers. Since we have found that there is a correlation between the decay time constant and the energy at which the ions were implanted into the sample, the computer then uses the decay time constant to determine the implantation energy, possibly employing stored tables of empirically derived data to perform a translation from one to the other.

In still other embodiments, a signal waveform is measured as described in the parent patent application (U.S. Ser. No. 08/885,786), i.e., using two independent lasers. The decay time constant of the waveform can be computed and processed in the manner described above to determine the energy at which the ions were implanted.

In still other embodiments, the apparatus can be modified to additionally measure the thickness of thin oxide (i.e. $SiO_2$) films that are grown on a silicon sample when the sample is subjected to high temperatures. For example, the computer can analyze the reflected probe beam (20" in FIG. 4) in the same way that reflected beams are analyzed in standard ellipsometers or reflectometers. This analysis permits simultaneous determination of ion implantation concentration and oxide film thickness. In other embodiments, sets of excitation sub-pulses having different wavelengths (e.g. 532 nm and 1064 nm) can be generated and used to simultaneously generate grating patterns in the sample being measured. In that case, the intensity of the diffracted signal beams can be analyzed to determine the species of the implanted ions. In other embodiments, the apparatus can be modified to simultaneously measure physical processes that result in phase gratings (e.g., excited charge carriers) and surface ripple (e.g., thermal processes) in the sample. For example, thermal processes that generate surface ripple in the sample will have a time dependence and diffraction efficiency that varies with the phase mask pattern (and thus the spatial periodicity of the grating pattern) used during the measurement. In contrast, the time dependance of non-diffusive processes, such as charge carrier lifetimes, is independent of the phase mask and grating patterns. Thus, these processes can be determined independently by measuring a sample at a number at different phase mask patters. In still other embodiments, a probe laser that generates a pulse having a long duration (e.g., several microseconds) relative to the lifetime of the charge carriers can be included in the optical system. This way, measurements can simultaneously be performed with probe pulses having different time durations and peak intensities. In still other embodiments the polarization of the diffracted probe pulse can be analyzed to determine certain properties of the sample, such as oxide film thickness and implant species.

There also exists other embodiments for processing the signal waveform to determine the concentration of implanted ions. For example, the signal waveform can be processed by plotting it and then determining the area underneath the plot. This area is then compared to values in a database to determine the ion concentration. In other embodiments, the signal waveform is fit to a function to determine its amplitude, which is then processed as described above. In still other embodiments, mathematical algorithms, such as algorithms based on kinetic modeling of a charge-carrier system, can be developed to relate the concentration of implanted ions to an amplitude of the signal waveform. Such algorithms would obviate the need for a database to determine the ion concentration.

In still other embodiments, laser beams that are not pulsed (i.e., continuous-wave excitation and probe beams) are used in the FWM arrangement to determine the concentration of ions in the sample. In this case, the amplitude of the diffracted signal beam correlates to the ion concentration. The signal beam, for example, may be detected using standard detection techniques known in the art, such as lock-in detection.

All references cited herein are incorporated herein by reference in their entirety and for all purposes to the same extent as if each individual publication or patent or patent application was specifically and individually indicated to be incorporated by reference in its entirety for all purposes.

Still other embodiments are within the scope of the following claims:

What is claimed is:

1. A method for determining a concentration of ions implanted in a material, comprising the steps of:

generating at least two excitation laser sub-pulses and a probe pulse from a single pulse emitted from a laser;

irradiating a region of the material with a grating pattern, formed by overlapping the at least two excitation laser sub-pulses to initiate a time-dependent response in the region;

diffracting the probe pulse off the region to generate at least one time-dependent signal beam;

detecting the at least one time-dependent signal beam to generate a signal waveform; and processing the signal waveform to determine the concentration of ions implanted in the material.

2. The method of claim 1, wherein the processing step includes determining a property of the signal waveform and then analyzing the property to determine the concentration of ions implanted in the sample.

3. The method of claim 2, wherein the property is an amplitude of the signal waveform.

4. The method of claim 2, wherein the processing step further includes comparing the property of the signal waveform to a database.

5. The method of claim 4, wherein the comparing step further includes comparing the property of the signal waveform to a database that correlates properties of previously measured signal waveforms to concentrations of ions implanted in materials to determine the concentration of ions implanted in the material.

6. The method of claim 5, wherein the property of the signal waveform is an amplitude.

7. The method of claim 1, wherein the processing step further includes analyzing the property with a mathematical algorithm to determine the concentration of ions implanted in the material.

8. The method of claim 1, wherein the processing step includes digitizing the signal waveform to generate a data set and then determining an amplitude of the signal waveform at a point in time by selecting a value from the data set.

9. The method of claim 1, wherein the processing step includes determining an area covered by a plot of the signal waveform.

10. The method of claim 9, wherein the processing step further includes comparing the area to a database.

11. The method of claim 10, wherein the comparing step further includes comparing the area to a database that correlates the area with the concentration of ions implanted in a material to determine the concentration of ions implanted in the material.

12. The method of claim 1, wherein the material contains silicon.

13. The method of claim 12, wherein the material is a polysilicon film.

14. The method of claim 12, wherein the material is a silicon wafer.

15. The method of claim 1, wherein an ion implanted in the material is an ion of an atom selected from the group consisting of arsenic, argon, boron, oxygen and phosphorous atoms.

16. A method for determining a concentration of ions implanted in a material, comprising the steps of:

generating a single laser pulse;

passing the single laser pulse through a phase mask to form at least two excitation sub-pulses and at least one probe pulse;

irradiating a region of the material with a grating pattern, formed by overlapping the at least two excitation least sub-pulses to initiate a time-dependent response in the region;

diffracting the probe pulse off the region to generate at least one time-dependent signal beam;

detecting the at least one time-dependent signal beam to generate a signal waveform; and processing the signal waveform to determine the concentration of ions implanted in the material.

17. The method of claim 1, wherein the processing step includes determining a property of the signal waveform and then processing the property to determine the concentration of ions implanted in the sample.

18. The method of claim 17, wherein the property is an amplitude of the signal waveform.

19. The method of claim 17, wherein the processing step further includes comparing the property of the signal waveform to a database.

20. The method of claim 19, wherein the comparing step further includes comparing the property of the signal waveform to a database that correlates properties of previously measured signal waveforms to concentrations of ions implanted in materials to determine the concentration of ions implanted in the material.

21. An apparatus for determining a concentration of ions implanted in a semiconduting material, comprising:

a laser for generating an excitation laser pulse and a probe laser pulse from a single laser pulse;

a first beam-delivery system for separating the excitation laser pulse into at least two excitation sub-pulses and then irradiating a region of the material with a grating pattern formed by overlapping the at least two excitation sub-pulses to initiate a time-dependent response in the region;

a second beam-delivery system for delivering the probe pulse to the sample such that the probe pulse diffracts off the region to generate a time-dependent signal beam;

a photodectector for detecting the time-dependent signal bean to generate a signal waveform; and a processor for processing the signal waveform to determine the concentration of ions implanted in the material.

22. The apparatus of claim 21, wherein the first beam-delivery system includes a phase mask that separates the excitation laser pulse into at least two sub-pulses.

23. The apparatus of claim 21, wherein the diffracting mask is a phase mask or an amplitude mask.

24. The apparatus of claim 21, wherein the processor is a computer that analyzes an amplitude of the signal waveform and compares the amplitude to a database to determine the concentration of ions implanted in the material.

25. The apparatus of claim 21, wherein the processor is a computer that determines an area covered by the signal waveform and compares the area to a database to determine the concentration of ions implanted in the material.

26. The apparatus of claim 21, wherein the excitation sub-pulses and the probe pulse are overlapped in time in the region.

27. The apparatus of claim 21, wherein the photodetector has a bandwidth of less than 1 MHz.

28. An apparatus for determining a concentration of ions implanted in a semiconducting material, comprising:

a laser for generating a single laser pulse;

a beam-delivery system comprising a phase mask that separates the single laser pulse into at least two excitation sub-pulses and a probe pulse, and a lens that focuses and overlaps at least two excitation sub-pulses and the probe pulse on the sample so that the excitation sub-pulses form a grating pattern that initiates a time-dependent response in the region and the probe pulse diffracts off the region to generate a time-dependent signal beam;

a photodetector for detecting the time-dependent signal beam to generate a signal waveform; and a processor for processing the signal waveform to determine the concentration of ions implanted in the material.

29. The apparatus of claim 28, wherein the diffracting mask is a phase mask or an amplitude mask.

30. The apparatus of claim 28, wherein the processor is a computer that analyzes an amplitude of the signal waveform and compares the amplitude to a database to determine the concentration of ions implanted in the material.

* * * * *